United States Patent [19]

Yoshida et al.

[11] Patent Number: 5,380,753
[45] Date of Patent: Jan. 10, 1995

[54] BATH AGENT

[75] Inventors: Shoji Yoshida, Nishinomiya; Kazumi Ogata, Toyonaka; Osamu Kawahira, Osaka, all of Japan

[73] Assignee: Senju Pharmaceutical Co., Ltd., Osaka, Japan

[21] Appl. No.: 39,996

[22] Filed: Mar. 30, 1993

[30] Foreign Application Priority Data

Apr. 10, 1992 [JP] Japan .................. 4-135519

[51] Int. Cl.$^6$ .................. A61K 31/34; C07D 305/12
[52] U.S. Cl. .................. 514/474; 549/315
[58] Field of Search .................. 549/315; 514/474

[56] References Cited

U.S. PATENT DOCUMENTS 4,361,515 11/1982 Terahara et al. .................. 549/292

OTHER PUBLICATIONS

Chemical Abstracts vol. 112 No. 22, #204,487e, Matsumoto et al, "Skin-lightening cosmetics containing (L-ascorbic acid)", 1989.

Primary Examiner—C. Warren Ivy
Assistant Examiner—Raymond Covington
Attorney, Agent, or Firm—Wenderoth, Lind & Ponack

[57] ABSTRACT

This invention relates to a bath agent containing sodium chloride and a compound represented by the formula

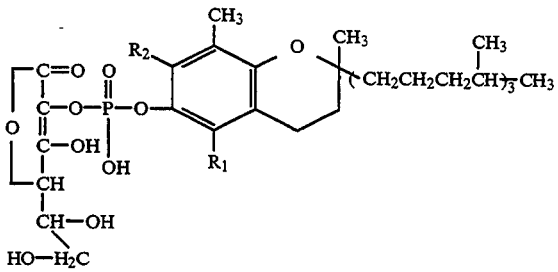

(in the formula $R_1$ and $R_2$ are the same or different, and are a hydrogen atom or a methyl group) or its salt.

This inventive bath agent is to eliminate and prevent skin itching and to prevent skin aging by preventing and removing effectively the free radical produced on the skin surface by ultraviolet rays.

3 Claims, No Drawings

BATH AGENT

BACKGROUND OF THE INVENTION

1. Field of the Invention

This invention relates to a useful bath agent having the effects of eliminating and preventing skin itch and preventing skin aging. More particularly, it relates to a bath agent which contains sodium sulfate and/or sodium chloride and a free radical inhibitor and which is useful for eliminating and preventing itching and for preventing the aging of skin by preventing and removing effectively the free radical produced on the skin surface.

2. Description of the Prior Art

There have been known various bath agents so far. For example, the bath agents added with sodium sulfate and sodium chloride for the purpose of keeping the skin warm have been used from old times. There is also known a bath agent compounded of proteinases to wash off the waste matter of skin and the skin keratin [KOKAX (First Publication) No. SHO 58-59909]. Moreover, there are known a bath agent compounded of galenica or galenical extract for the purpose of antiphlogistic effect and a bath agent compounded of kojic acid, its salt or L-ascorbic acid-2-magnesium phosphate For the purpose of preventing spots and freckles and becoming fair-complexioned [KOKAI (First Publication No. HEI 3-127724]

On the other hand, the free radical which produced on the skin surface by ultraviolet rays said to be the cause of itching or skin aging and progress into skin cancer in the worst case. Originally, there exists an enzyme, superoxide dismutase (SOD), in the skin which prevents the production of free radical on the skin surface. However, in case of the exposure to excessive ultraviolet rays or in case of the elderly having less SOD, the production of free radical cannot be prevented effectively. Therefore, in such a case a drug which removes the free radical produced on the skin surface is required.

Under such a situation, if there is a bath agent which has an action of preventing and removing effectively the free radical produced on the skin surface by ultraviolet rays and which can be used easily, it is considered to be convenient.

Generally, however, many free radical inhibitors are insoluble in water (for example, tocopherol, BHT, BHA) and water-soluble free radical inhibitors are hardly known. Although ascorbic acid, cystein, and glutathione which are water-soluble have strong reducing action, their inhibitory action is very weak if they have free radical-inhibitory action. Therefore, the action cannot be said to be fully satisfactory for the removal of free radical produced on the skin surface, which is the object of this invention.

Accordingly, bath agents having satisfactory free radical-removing effect [lave not been known so far under present conditions.

So the inventors made earnest investigation looking for useful bath agents to prevent and remove effectively the free radical produced on the skin surface. Consequently, the inventor unexpectedly found it possible to prevent and remove effectively the free radical produced on the skin surface by the combined use with sodium sulfate and/or sodium chloride and L-ascorbic acid tocopherolphosphate diester. This invention has been completed based on this new knowledge.

SUMMARY OF THE INVENTION

This invention relates to a useful bath agent which is characterized by containing sodium sulfate and/or sodium chloride and a compound represented by the following formula ( I )

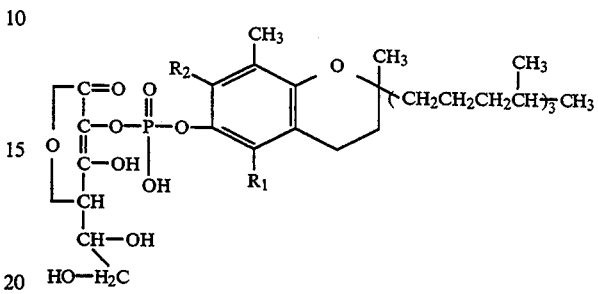

(in the formula $R_1$ and $R_2$ are the same or different, and are a hydrogen atom or a methyl group) or its salt and which is able to prevent and remove effectively the free radical produced on the skin surface.

DETAILED DESCRIPTION OF THE INVENTION

The compound which is incorporated in the bath agent of tills invention and represented by formula (I) (hereinafter sometimes referred to "L-ascorbic acid-tocopherolphosphate diester") or its salt is a compound which the inventors previously invented, and it can properly be manufactured, For example, by time methods mentioned in KOHKOKU (Second Publication) No. HEI 2-44478 which corresponds to U.S. Pat. No. 4,564,686 and KOKAI (First Publication) No. SHO 62-205091 which corresponds to U.S. Pat. No. 4,914,197 or in accordance with them.

As to time efficacy of a compound represented by Formula (I), the anti-cataract action [KOHKOKU (Second Publication No. HEI 2-44478 which corresponds to U.S. Pat. No. 4,564,686], the antiinflammatory action [KOHKOKU (Second Publication) No. HEI 1-27044] and so forth have already been known. The alkali metal salts are water-soluble having the surface-active action, and their stability in water is also excellent.

However, it has not been known yet that a bath agent in which the compound represented by formula (I) is used together with sodium sulfate and/or sodium chloride can effectively prevent and remove the free radical produced on the skin surface and thereby it is effective in preventing and removing an eliminating and in preventing skin aging.

The excellent effect of this inventive bath agent has not been attained until the compound represented by formula (I) was used together with sodium sulfate and/or sodium chloride.

L-ascorbic acid-tocopherolphosphate diester compounds or their salts incorporated in this inventive bath agent may be used by combining one or more kinds of them at the proper ratio according to the object. As for their salts, any salt will do provided that it is pharmacologically acceptable and water-soluble. For example, alkali metal salts such as sodium salt and potassium salt can be used suitably for the purpose of this invention.

The concentration of L-ascorbic acid-tocopherol-phosphate diester compound or its salt incorporated in this invented bath agent is suitably selected according to the kind of compound or the dosage form of bath agent, but it is good usually in about 0.001–5.0 (W/W) % and desirably in 0.01–0.5 (W/W) % or so.

Inorganic salts—sodium sulfate and sodium chloride—which are incorporated in this inventive bath agent are used alone or together, respectively.

As for sodium sulfate, an inorganic salt, incorporated in this inventive bath agent, any of its anhydride ($Na_2SO_4$), monohydrate ($Na_2SO_4.H_2O$) and decahydrate ($Na_2SO_4.10H_2O$) can be used suitably. Moreover, these may be used alone or more kinds may be properly used together.

The concentrations of sodium sulfate and sodium chloride in the bath agent are different according to the dosage form of bath agent and single or joint use of these inorganic salts, but they can be adjusted to the optional concentration in which the quantities of the compound represented by formula (I) and other bases are deducted from the quantity of this bath agent. For instance, as to the concentrations in case of using these jointly, they are desirably 40–70 (W/W) % or so in sodium sulfate and 30–70 (W/W) % or so in sodium chloride, but they are not always limited to these figures.

This inventive bath agent can take various dosage forms such as liquid and jelly-like forms. Considering the convenience for dealing, however, it is usually desirable to make the dosage forms such as powders, granules, tablets, and effervescent tablets. These preparations can be manufactured properly by the conventional methods used for the manufacture of bath agents. Besides, it is convenient for dealing to seal hermetically this inventive bath agent in proper bags and containers such as polyethylene-coated aluminium bags and polyethylene containers.

A dose of this inventive bath agent given in the bath is properly selected according to the kinds of active constituents and their concentrations, dosage forms of bath agents, the age of bathers, their skin conditions, and the bath temperature. For instance, about 5–60 g per bath of 150-1 are usually good and desirably about 10–40 g are good. However, the dose is not always limited to these figures.

In this inventive bath agent, moisture-retention agent, enzyme agent, binder, disintegrator, effervescing agent, dispersing agent, coloring matter, aromatic, surfactant, buffer, stabilizer, pH-adjusting agent, etc. which have hitherto been used as the ingredients of bath agent can be incorporated properly at the commonly-used concentrations.

Furthermore, in this inventive bath agent, upon necessity other ingredients having free radical-inhibiting action and different kinds of efficacious ingredients (hoe spring ingredients etc.) can be contained properly, unless they are against the purpose of this invention.

EXAMPLES

The following examples are further illustrative of the present invention.

The abbreviations of compound of formula (I) used in the undermentioned examples express the following compounds, respectively:

α-EPC ($R_1 = R_2$ = methyl group)
β-EPC ($R_1$ = methyl group, $R_2$ = hydrogen atom)
γ-EPC ($R_1$ = hydrogen atom, $R_2$ = methyl group)
δ-EPC ($R_1 = R_2$ = hydrogen atom)

EXAMPLE 1

| Sodium sulfate | 1 kg |
|---|---|
| Jasmine | proper quantity |
| δ-EPC dipotassium salt | 1 g |

Mix the above materials uniformly, fill each 30 g per wrapper in a polyethylene-coated aluminum bag after drying and seal hermetically to make a bath agent.

EXAMPLE 2

| Sodium sulfate | 700 g |
|---|---|
| Sodium chloride | 200 g |
| Potassium chloride | 100 g |
| α-EPC dipotassium salt | 5 g |
| Maleic anhydride | 9.8 g |
| Sodium hydrogencarbonate | 17 g |
| Aromatic | proper quantity |
| Coloring agent | proper quantity |

Mix the above materials with ethanol, fill each 30 g per wrapper in a polyethylene-coated aluminium bags after drying and seal hermetically to make a bath agent.

Effect

When this bath agent was applied to a 60 year-old male who sometimes complained of an unaccountable itch on his back, itching left him after bathing. As another case, when the bath agent was applied to a 25 year-old female who had had an itch on the whole body after swimming, itching was gone after bathing and the agent proved to be effective.

EXAMPLE 3

| α-EPC monopotassium salt | 2 g |
|---|---|
| Sodium chloride | 600 g |
| Sodium sulfate, anhydrous | 18 g |
| Potassium chloride | 0.5 g |
| Sodium hydrogencarbonate | 0.5 g |
| Magnesium chloride | 260 g |
| Calcium chloride | 36 g |
| Boric acid | 0.3 g |
| Borax | 0.1 g |
| Sodium edetate | 0.13 g |

Mix the above materials uniformly, fill in a polyethylene container holding, after drying and put about 30 g in a 150-1 bathtub.

What is claimed is:

1. A bath agent containing sodium sulfate and/or sodium chloride and a compound represented by the following formula (I)

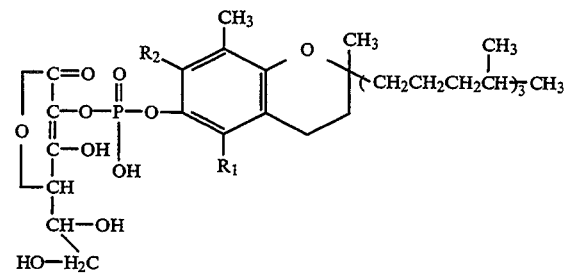

wherein $R_1$ and $R_2$ are the same or different, and are a hydrogen atom or a methyl group or a pharmacologically acceptable salt thereof.

2. The bath agent as claimed in claim 1 in which the concentration of the compound represented by formula (I) or its salt is 0.001 to 5.0 (W/W) %.

3. A method for eliminating and preventing skin itch and preventing skin aging which comprises applying to the skin of a patient in need of such treatment a bath agent as defined in claim 1.

* * * * *